United States Patent [19]

Katz

[11] Patent Number: 5,071,879

[45] Date of Patent: * Dec. 10, 1991

[54] SYSTEMIC ANTIVIRAL TREATMENT

[75] Inventor: David H. Katz, La Jolla, Calif.

[73] Assignee: Lidak Pharmaceuticals, La Jolla, Calif.

[*] Notice: The portion of the term of this patent subsequent to Oct. 17, 2006 has been disclaimed.

[21] Appl. No.: 431,304

[22] Filed: Nov. 2, 1989

Related U.S. Application Data

[63] Continuation-in-part of Ser. No. 345,084, Apr. 28, 1989, Pat. No. 4,874,794.

[51] Int. Cl.$^5$ .............................................. A61K 31/045
[52] U.S. Cl. ................................................... 514/724
[58] Field of Search ........................................ 514/724

[56] References Cited

U.S. PATENT DOCUMENTS 4,186,211 1/1980 Debat .................................. 424/343
4,513,008 4/1985 Revici et al. ......................... 514/560

FOREIGN PATENT DOCUMENTS 2569108 2/1986 France .
8807866 10/1988 World Int. Prop. O. .
9004388 5/1990 World Int. Prop. O. .

Primary Examiner—Stanley J. Friedman
Attorney, Agent, or Firm—Grant L. Hubbard

[57] ABSTRACT

Systemic antiviral treatment using a narrow class of aliphatic straight-chain saturated monohydric alcohols which have from 20 to 26, preferably 22 to 26, carbons in the chain in physiologically compatible compositions for injection or trans-mucus membrane introduction into humans and other animals is disclosed.

18 Claims, 1 Drawing Sheet

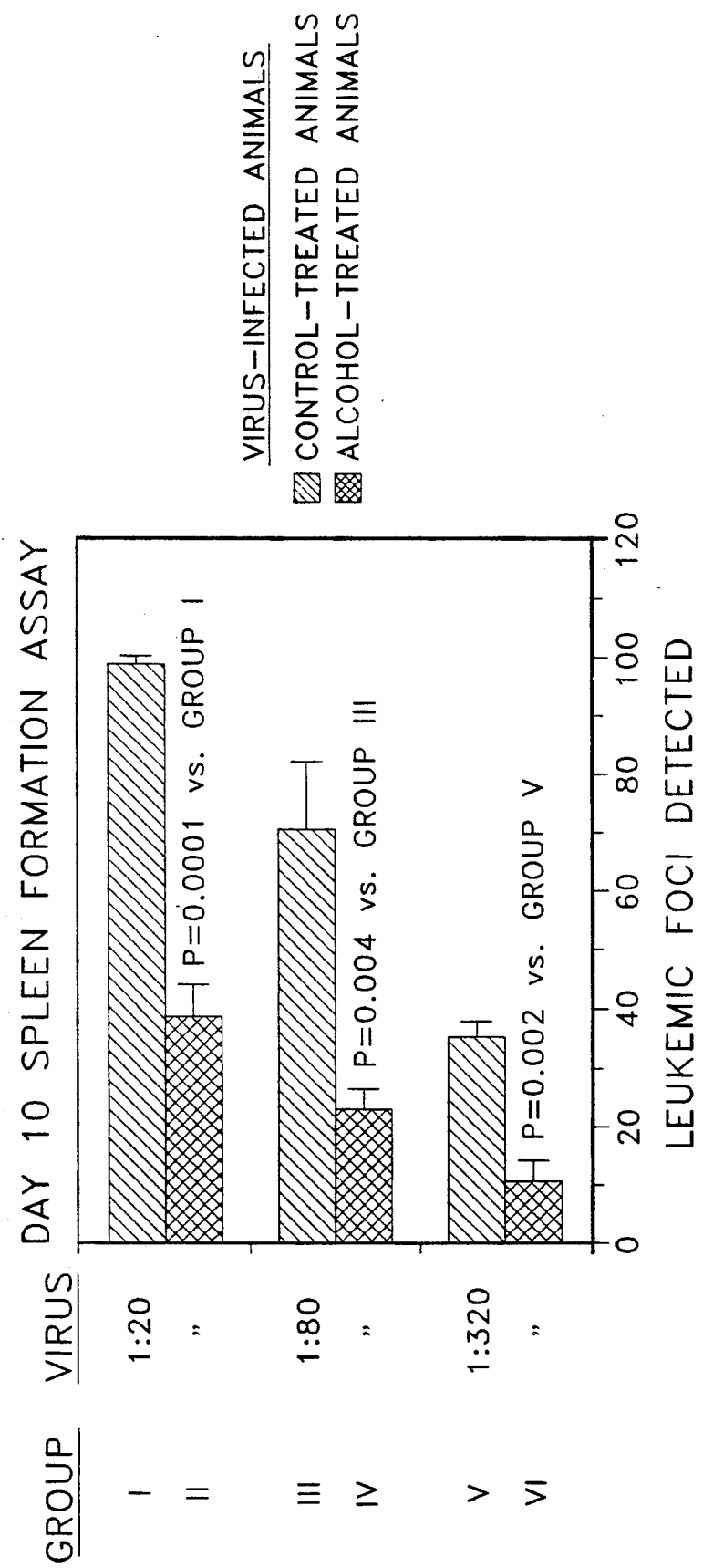

SYSTEMIC ANTIVIRAL TREATMENT

CROSS-REFERENCE TO RELATED APPLICATION

This is a continuation-in-part of the present inventor's co-pending patent application Ser. No. 07/345,084, filed Apr. 28, 1989, INFLAMMATORY DISEASE TREATMENT, now U.S. Pat. No. 4,874,794, to which priority is claimed.

FIELD OF THE INVENTION

This invention relates to alcohol-containing compositions which are useful in the systemic treatment of various virus infections. More specifically, the present invention relates to a systemic antiviral treatment using a narrow class of aliphatic straight-chain saturated monohydric alcohols which have from 20 to 26, preferably 22 to 26, carbons in the chain.

BACKGROUND OF THE INVENTION

It is well known that certain selected alcohols have some physiological activity. It is known, for example, that 1-triacontanol stimulates the growth of plants, see, e.g. Ries, Stanley K. and Sweeney, Charles C., U.S. Pat. No. 4,150,970. Interestingly, the C-30 alcohol triacontanol appears to possess this physiological activity, and the C-28 and C-32 do not possess such physiological activity, or at least have very much less physiological activity in plant growth, see, e.g., the patents and publications of Ries et al., ibid, and of Ashmead, Harvey H., Weleber, Andrew J., Laughlin, Robert G., Nickey, Donald O. and Parker, Dane. K, and Ohorogge, Alvin J.

Triacontanol has also been reported to accelerate the decomposition of sewage and reduce $H_2S$, Starr, Jerry, U.S. Pat. No. 4,246,100.

Beeswax comprises, inter alia, esters of long-chain aliphatic alcohols having chain lengths in the area of interest, and it is known to obtain such alcohols by hydrolysis of beeswax. Beeswax has been used since antiquity in a great variety of cosmetic and therapeutic applications, as a base for lipstick, in lotions and creams, as an emollient and as a constituent in therapeutic products for topical and membrane application. Various constituents of beeswax and products derived from beeswax have also been used in cosmetic and therapeutic applications. For example, Slimak, Karen M., U.S. Pat. No. 4,793,991, describes a hypoallergenic cosmetic comprising single plant source beeswax. Gans, Eugen, Nacht, Sergio and Yeung, David have described the use of the non-polar saturated straight chain C-21 to C-33 hydrocarbon fraction of beeswax in the treatment of inflammatory skin disorders, U.S. Pat. No. 4,623,667.

The mechanism of the rather diverse and unpredictable physiological effects of the various alcohols are, at best, poorly understood, and studies are not generally definitive. There appears to some interaction of certain n-alkanols with lipid bilayer membranes, Westerman, P. W., Pope, J. M., Phonphok, N., Dan, J. W., Dubro, D. W., Biochim Biophys Acta(NETHERLANDS) 939, 64–78 (1988), and studies have been conducted respecting the partitioning of long-chain alcohols into lipid bilayers, Franks N. P. and Lieb W. R., *Proc. Natl. Acad. Sci. USA* 83 5116–20 (1986); cholesterol solubility of n-alkanols, Pal S. and Moulik S. P., *Indian J Biochem Biophys* 24–8 (1987); neurological effects of certain long-chain alcohols, Natarajan V. and Schmid H. H., *Lipids* 12 128–30 (1977); Snider S. R., *Ann Neurol* 16 723 (1984); Borg J., Toazara J., Hietter H., Henry M., Schmitt G., Luu B., *FEBS Lett* 213 406–10 (1987).

Levin, Ezra reported that tetracosanol, hexacosanol, octacosanol and triacontanol and their esters improved physical performance of athletes and disclosed compositions comprising such alcohols and esters in vegetable oil bases for oral ingestion, U.S. Pat. No. 3,031,376.

An incidental disclosure of a composition intended for topical application comprising a major portion liquified gaseous propellant and a minor portion of a mixture of C-12 to C-30 fatty alcohols which were used simply to mark the areas of application of the aerosol is contained in U.S. Pat. No. 3,584,115 to Gebhart.

Clark, U.S. Pat. No. 4,670,471 discloses the use of triacontanol, in a suitable carrier, as a treatment for inflammatory disorders such as herpes simplex, eczema, shingles, atopic dermatitis, psoriasis, etc. Clark performed experiments with the compositions of the type disclosed by Gebhart, U.S. Pat. No. 3,584,115 comprising an aerosol and a mixture of triacontanol and palmitic acid, which Clark indicates to be as effective as pure triacontanol, and concluded that the aerosol carrier destroyed the effect of triacontanol and that a hydrophilic carrier for triacontanol was necessary to achieve the desired anti-inflammatory effect. There is some reason to believe that Clark's composition was simply saponified beeswax which would contain triacontanol and palmitic acid, as Clark indicates, but which would also contain, as substantial constituents, hexacosanolic acid and various hydrocarbons. Results gas chromatographic-mass spectrum analysis of various compositions believed to have been used by Clark were not definitive, but suggested that at least some such compositions were very complex mixtures, some of which may be lower alkanes, esters, acids or alcohols. Whether or not these were found by Clark to be effective anti-inflammatory compositions is not known. McKeough, Mark and Spruance, S. L. evaluated the efficacy of 5% triacontanol in a branch chain ester base in the treatment of HSV-1 dorsal cutaneous infection in guinea pigs and concluded that the active ingredient in triacontanol is the long chain hydrocarbon (unpublished report in the file of U.S. Pat. No. 4,670,471).

Revici, Emanuel, Sherwood, Bob E., Benecke, Herman P., Rice, John M., and Geisler, Richard W., U.S. Pat. No. 4,513,008, disclose a method of inactivating enveloped virus using C-20 to C-24 polyunsaturated acids, aldehydes or alcohols having 5–7 double bonds, and references disclosures by Sands et al. *Antimicrobial Agents and Chemotherapy* 15, 67–73 (1979) (antiviral activity of C-14 to C-20 unsaturated alcohols having 1–4 double bonds), Snipes et al., *Antimicrobial Agents and Chemotherapy* 11, 98–104 (1977) (C-20 tetraenyl alcohol having low activity) and *Symp. Pharm. Effects Lipids (AOCS Monograph N.5)* 63–74 (1978) (suggesting lower antiviral activity for saturated long-chain alcohols).

Katz, Martin and Neiman, Herbert M, U.S. Pat. No. 3,592,930, disclose a medicant vehicle containing from 15 to 45 parts of saturated fatty alcohol from 16 to 24 carbons, along with glycol solvent, plasticizer, penetrant and adjuvant which is used as a carrier for antibiotics, steroids, antihistamines, etc. Ryde, Emma Marta and Ekstedt, Jan Erik, U.S. Pat. No. 3,863,633, disclose a composition for topical treatment of the eye which comprises a lipophilic substance, a hydrophilic swellable polymer and from 10 to 80% C-12 to C-22 surface active alcohols such as 1-docosanol, 1-hexadecanol, 1-octadecanol and 1-eicosanol which serve as a stabilizer for the mixture.

The content of the prior art and the corresponding skill of the art, relative to topically administered compositions, may be summarized as follows: short-chain alcohols, i.e. under about 16 carbons, tend to be irritants while longer chain alcohols, particularly the aliphatic alcohols tend to be non-irritating (Katz et al., supra). 1-Triacontanol, a 30-carbon unsaturated aliphatic alcohol, in a suitable hydrophilic carrier has (or, may have, depending upon the precise compositions used by Clark) value in treating inflammatory conditions of the skin (Clark, supra). Shorter chain C-10 to C-14 aliphatic alcohols demonstrate low level in vitro virucidal characteristics, while C-18 alcohols show no discernable virucidal activity in vitro (Snipes, supra). Polyunsaturated C-20 to C-24 alcohols inactive enveloped virus (Revici et al., supra). C-16 to C-24 aliphatic alcohols are useful as stabilizers in carrier compositions for drugs having diverse physiological activity.

Respecting aliphatic alcohols, one would predict from the studies of Snipes and Clark that, in the continuum of aliphatic alcohols from C-10 to C-30 virucidal activity, at a very low level, may appear (if in vitro studies may be used to predict in vivo results) in C-10 to C-14 alcohols (which would also be irritants as reported by Katz), that virucidal activity dissapears in the C-16 to C-28 range and then appears uniquely (if Clark's compositions were pure triacontanol or mixtures of triacontanol with palmitic acid as he indicates) with the C-30 alcohol 1-triacontanol, which has been shown to have unique physiological effects in plant treatment.

Even considering the possible ambiguity of Clark's compositions, one would not predict any significant virucidal activity for aliphatic alcohols in the C-20 through C-28 chain length.

Notwithstanding the negative teachings of the prior art, the inventor has previously discovered that a composition, in which the active constitute consists essentially of C-20 to C-26, and preferably C-22 to C-26 aliphatic alcohols, e.g. docosanol, tetracosanol and hexacosanol, is an effecting topical anti-inflammatory, (see the present inventor's co-pending patent application Ser. No. 07/345,084, filed Apr. 24, 1989, INFLAMMATORY DISEASE TREATMENT, to which priority is claimed to the extent of the disclosure therein), and has now determined that this class of compounds may be used, in suitable carrier compositions, in the systemic treatment of virus-induced disease and in the prevention or inhibition of infection by disease-causing virus.

SUMMARY OF THE INVENTION

The present invention is embodied in methods for preventing, inhibiting and treating virus diseases in humans or other animals, comprising intravenous, intramuscular, transdermal or oral introduction into the human or other animal to be treated of a composition consisting of one or more of C-20 to C-26 aliphatic alcohols in a physiologically compatible carrier, and to compositions suitable for carrying out such methods.

BRIEF DESCRIPTION OF THE DRAWING

FIG. 1 depicts data showing the inhibition of Friend virus-induced erythroleukemia.

DESCRIPTION OF THE PREFERRED EMBODIMENTS

The method may be carried out using compositions in which the sole physiologically active agent(s) is the C-20 to C-26 aliphatic alcohol, or comparable compositions which may also include other physiologically active constituents which do not interfere with the efficacy of the C-20 to C-26 alcohols. Corresponding low molecular weight ethers of these alcohols, e.g. methyl-, ethyl-, propyl-, etc., ether derivatives of these alcohols, and corresponding low-molecular-weight ester derivatives, e.g. formyl-, acetyl-, propyl-, etc., ether derivatives of these alcohols are regarded as less preferred possible equivalents of the alcohols of this invention.

The composition of the carrier is not critical so long as the carrier is physiologically compatible with the blood and tissues of the human or other animal to be treated and is substantially free from any interfering physiological effect.

Compositions suitable for intravenous or intramuscular injection into the human or animal patient consist essentially of one or more aliphatic alcohols having from 20 to 26 carbons in the aliphatic chain of the alcohol(s) in a suitable carrier. For example, a suspension of from 0.1 mg/ml to 300 mg/ml of the indicated alcohol(s) suspended in a carrier solution of isotonic sodium chloride solution containing a suitable preservative, such as 0.1 to 1.5% benzyl alcohol, stabilizers such as from 0.25 to 1% carboxymethylcellulose sodium and 0.005 to 0.1% polysorbate 80, and sufficient sodium hydroxide or hydrochloric acid to adjust the pH to 5.0 to 7.5, all percentages by weight, may be used either intravenous or intramuscular injection.

Another composition suitable for intravenous or intramuscular injection into the human or animal patient may consist essentially of one or more aliphatic alcohols having from 20 to 26 carbons in the aliphatic chain of the alcohol(s) in a suitable carrier in suspension of from 0.1 mg/ml to 300 mg./ml of such alcohol(s) suspended in a carrier solution of alcohol (1–10%), glycerin (10–20%) and water (balance 70–89%), along with suitable preservative.

Such compositions may be injected in suitable amounts to provide a dose to the patient of from 0.1 mg/50 kg body weight to 2 gm/50 kg body weight. It is desirable to achieve and maintain a level of the specified alcohol(s) in the body in the range of at least about 0.1 mg/kg of body weight.

The alcohol(s) to which this invention is directed may effectively be introduced through the mucus membrane system of the human or animal patient. Such introduction may be, for example, through the vaginal, anal, oral or nasal membranes. The above liquid compositions which consist essentially of one or more aliphatic alcohols having from 20 to 26 carbons in the aliphatic chain of such alcohol(s) in a suitable liquid carrier may, for example, be used for trans-mucus membranal introduction of such alcohol(s) into the circulatory system of the human or animal to be treated by, for example, introducing such liquid as an aerosol into the oral or nasal passages or as a liquid into the vaginal or anal passage of the body where these compounds inactivate virus locally, inhibit the passage of virus into the membrane, and pass through the membrane into the circulatory system of the patient where the compounds act as inhibitors of viral activity and infectivity and inactivate virus. In the latter applications, however, gels, creams or suppositories are more conveniently used.

In one convenient embodiment, the method of the invention comprises a composition consisting essentially of one or more aliphatic alcohols having from 20 to 26 carbons in the aliphatic chain of such alcohol(s) into the vagina, where it will inhibit the activity of the sperm and interfere with fusion of the sperm cell with the female egg cell. The alcohol composition of interest may, of course, be used in connection with a diaphragm or other contraceptive device if desired.

As indicated above, the alcohols of interest here will serve as contraceptive compositions. The mode of action has not been fully explored, but it is believed that these alcohols reduce the activity and viability of sperm and inhibit or prevent the sperm from attaching to and penetrating the egg, thus preventing fertilization.

Likewise, the alcohol-containing composition may be introduced through the anus where it also inactivates virus, inhibits the passage of virus into the membrane, and passes through the membrane into the circulatory system of the patient where it acts as an inhibitor of viral activity and infectivity and inactivates virus in the circulatory system and cells nourished by the circulatory system. The specified alcohol(s) may be in any physiological acceptable form such as in cream or suppository compositions. An exemplary suppository may consist essentially of a composition consisting essentially of one or more aliphatic alcohols having from 20 to 26 carbons in the aliphatic chain of such alcohol(s) alone or in a concentration of from 0.05 mg alcohol(s)/gm of carrier to 400 (or higher) mg alcohol(s)/gm of carrier. Cocoa butter is a commonly used suppository carrier component, alone or in mixture with, for example, tartaric acid and malic acid. Polyethylene glycols of suitable molecular weight are also suitable suppository carriers. Suppositories may also include a preservative such as methylparaben or benzethonium chloride, and such acid or base components as are desired to adjust the pH to the range of about pH 5 to pH 7.5. Any of the above, or other, suitable suppository carrier compositions may be used with composition consisting essentially of one or more aliphatic alcohols having from 20 to 26 carbons in the aliphatic chain of such alcohol(s) to form a suitable contraceptive and/or anti-viral suppository. The suppository, to be commercially and aesthetically acceptable, must be a solid at ambient room temperature, i.e. generally in the range of about 27° C., and must melt at or slightly below normal body temperature, i.e. in the general range of about 37° C. These temperatures are, of course, only general ranges, and the precise melting point is not critical.

Trans-membranal introduction of such alcohol(s) may be accomplished by introducing small amounts of such alcohols neat, but such introduction is difficult to control and not efficient.

Cream and gel compositions consisting essentially of one or more aliphatic alcohols having from 20 to 26 carbons in the aliphatic chain of such alcohol(s) in concentrations of from about 0.1 mg/ml to 300 mg/ml (or higher) in a suitable cream or gel carrier may also be used effectively. Such a gel may, for example, comprise a suspension agent such as Carbomer ® polyacrylic acid cross-linked with allyl sucrose, polyethylene glycol, water and suitable preservatives. A suitable cream base may, for example, comprise white petrolatum, polyoxyethylene stearate, cetyl alcohol, stearyl alcohol, propylene glycol, isopropyl myristate, sorbitan monooleate and water along with suitable preservatives adjusted to a pH of from pH 5 to pH 7.5.

The alcohols of interest here may also be introduced for trans-membranal passage into the human or animal patient's circulatory system, as well as a prophylaxis against infection from airborne virus, through inhalation of a composition consisting essentially of one or more aliphatic alcohols having from 20 to 26 carbons in the aliphatic chain of such alcohol(s) in a suitable physiologically acceptable carrier. The liquid compositions mentioned before may, for example, be packaged in a nebulizer and introduced through nasal or oral passages in the customary manner. An exemplary composition consisting essentially of one or more aliphatic alcohols having from 20 to 26 carbons in the aliphatic chain of such alcohol(s) suspended in aerosol propellant such as trichloromonofluoromethane and/or dichlorodifluoromethane, along with diluents, preservatives, pH adjusting reagents, etc. The exemplary aerosol composition delivers essentially neat alcohol(s) to the mucus membrane. An exemplary ear drop composition delivers essentially neat alcohol(s) to the tympanic membrane. Comparable liquid drops may be applied using appropriate droppers to the eyes, ears and mouth for application to and passage through the membranes in these respective organs.

All trans-membranal compositions may, in addition to other ingredients, may also include penetration enhancers. A number of such enhancers are known as penetration enhancers and may be used in the compositions of this invention. One such vehicle is dimethyl sulfoxide, which is described in U.S. Pat. No. 3,551,554. Other such penetration enhancers are disclosed in U.S. Pat. Nos. 3,989,816; 3,991,203; 4,112,170; 4,316,893; 4,415,563; 4,423,040; 4,424,210; 4,444,762, sometimes referred to as Azone ®.

The anti-viral effectiveness of these alcohols has been established in in vitro tests, as demonstrated in the following example.

EXAMPLE 1

Ecotropic Virus

A composition a composition consisting essentially of aliphatic alcohols having 22 carbons in the aliphatic chain in micelle suspension, 600 µg alcohol/ml PBS buffer, was introduced into cultures of LP-BM 5 MuLV ecotropic virus, 1000 PFU/ml, and the percent of virus inhibition, as compared with controls continuing only PBS buffer, indicated by cell-fusion activity and cell plaque count, using XC indicator cells, was determined. The following table shows the viral inhibition as a function of concentration of the specified alcohols:

TABLE I

| LP-BM 5 input PFU/ml | Percent LP-BM 5 Virus Inhibition as a function of C-22 Alcohol Concentration (µg/ml) ($10^2$ input) | | | | |
|---|---|---|---|---|---|
| | 60 | 6 | 0.6 | 0.06 | 0 (Control) |
| 100 | 89 | 40 | 22 | 7 | 0 |

EXAMPLE 2

Ecotropic Virus

The effect of the C-20 to C-26 alcohols of this invention on ecotropic virus was further confirmed and compared with AZT.

TABLE II

| LP-BM 5 PFU/ml | Drug Concentration μg/ml | | | | |
|---|---|---|---|---|---|
| | 500 | 50 | 5 | 0.5 | medium |
| $10^3$ Input | Plaques/culture | | | | |
| C-22 Alcohol | 401 ± 5 | 562 ± 11 | 561 ± 50 | 703 ± 88 | 817 ± 14 |
| % decrease | 51 | 31 | 31 | 14 | 0 |
| AZT | 43 ± 6 | 131 ± 10 | 382 ± 59 | 657 ± 24 | 762 ± 43 |
| % decrease | 94 | 83 | 50 | 14 | 0 |
| Control (alcohol) | 733 ± 39 | 710 ± 72 | 700 ± 7 | 823 ± 14 | 702 ± 43 |
| % decrease | 0 | 0 | 0 | 0 | 0 |
| $10^2$ Input | | | | | |
| C-22 Alcohol | 13 ± 2 | 72 ± 24 | 84 ± 12 | 110 ± 2 | 131 ± 10 |
| % decrease | 90 | 45 | 36 | 19 | 0 |
| AZT | 5 ± 3 | 23 ± 5 | 43 ± 3 | 34 ± 3 | 108 ± 2 |
| % decrease | 95 | 79 | 60 | 69 | 0 |
| Control (alcohol) | 106 ± 6 | 106 ± 4 | 114 ± 7 | 99 ± 2 | 130 ± 11 |
| | 18 | 18 | 12 | 24 | 0 |

EXAMPLE 3

The effect of C-20 to C-26 alcohols on Friend virus-induced leukemia was investigated using the spleen focus formation assay (Virology 24:513, 1964). Balb/c mice were injected with 0.5 ml of the indicated dilution of virus. The animals were then injected intravenously with 1 ml of either a control solution or a solution containing 0.5 mg C-20 to C-26 alcohols on days 0, 1 and 2 of the experiment. On day 10 of the experiment, the animals were killed and their spleens placed into Bouin's fixative. The number of macroscopic leukemic cell foci in each of the spleens were then counted. The data are depicted in FIG. 1 as the geometric means and standard errors, with Groups I and II having 6 animals each, and 5 animals being in each of the remaining groups.

The discovery that these alcohols, which are naturally occurring and are essentially non-toxic in concentration ranges of interest have significant anti-viral effect is considered to be of major import inasmuch as the way is open to providing a safe and effective method for the treatment for virus diseases and for preventing or at least significantly reducing the likelihood of virus infection to the human or other animal patient, without any significant side effects and without the need for as intense monitoring by the treating physician as is required with inherently toxic compounds.

As a treatment for acquired immunodeficiency syndrome (AIDS), as a method for prophylactic treatment of persons exposed to AIDS and/or carrying AIDS virus but without demonstrating AIDS symptoms, and as methods and compositions for preventing or reducing the risk of infection by AIDS and virus-induced diseases, the present invention is regarded as a significant improvement.

Another important aspect of the invention is that it may provided a safe and effective mode of treatment of diseases resulting from infection of the patient with such lipid-containing virus as HTLV-1, HSV-1, HSV-2, cytomegalovirus (CMV), Epstein-Bar (EBV), and influenza viruses.

The risk of infection by such viruses as HIV, HSV-1, HSV-2, CMV, EBV, influenza viruses and other viruses which are communicated by personal contact, contact with contaminated blood or tissue or laboratory instruments or devices, aerosol transmission, etc., may be substantially reduced by the methods and compositions of the present invention.

It is believed that another mode of action of the alcohols of this invention is in the inhibition or prevention of malignant growth and/or metastasis. If, for example, cancer cells cannot metastasize, or the rate of metastasis is reduced, then the spread of cancer may be blocked or reduced. Significant inhibition of cancer cell metastasis coupled with natural or drug-induced death or destruction of existing cancerous cells will lead to partial or total remission of the disease. The same principle applies, of course, to any disease which is propagated by cell metastasis. Accordingly, the present invention is considered useful in the treatment of non-virus-induced disease and diseases which are not dependent upon viral replication but which are spread by metastasis.

It will be readily understood from the foregoing that the essential constituent(s) of the compositions useful in the present method is one or more aliphatic alcohols having from 20 to 26 carbons in the aliphatic chain of the alcohol(s), and that the composition of the carrier is non-critical and subject to great variation.

INDUSTRIAL APPLICATION

This invention is useful in treating and suppressing virus-induced diseases of humans and other animals.

What is claimed is:

1. A method of treating or preventing disease in humans or other animals, comprising introducing into the circulatory system of the human or other animal to be treated a composition consisting essentially of at least one C-20 to C-26 aliphatic alcohol in a physiologically compatible carrier.

2. A method of treating or preventing disease in humans or other animals, comprising introducing into the circulatory system of the human or other animal to be treated by intramuscular injection a composition consisting essentially of at least one C-20 to C-26 aliphatic alcohol in a physiologically compatible carrier.

3. A method of treating or preventing disease in humans or other animals, comprising introducing into the circulatory system of the human or other animal to be treated by transmucus membranal penetration a composition consisting essentially of at least one C-20 to C-26 aliphatic alcohol in a physiologically compatible carrier.

4. A method of treating or preventing disease in humans or other animals, comprising introducing into the human or other animal to be treated by transdermal penetration of a composition consisting essentially of at least one C-20 to C-26 aliphatic alcohol in a physiologically compatible carrier.

5. A method of preventing or inhibiting virus infection of humans or other animals, comprising introducing into the circulatory system of the human or other animal to be treated a composition consisting essentially of at least one C-20 to C-26 aliphatic alcohol in a physiologically compatible carrier.

6. A method of preventing or inhibiting virus infection of humans or other animals, comprising introducing into the circulatory system of the human or other animal to be treated by intramuscular injection a composition consisting essentially of at least one C-20 to C-26 aliphatic alcohol in a physiologically compatible carrier.

7. A method of preventing or inhibiting virus infection of humans or other animals, comprising introducing into the circulatory system of the human or other animal to be treated by transmucus membrane penetration a composition consisting essentially of at least one C-20 to C-26 aliphatic alcohol in a physiologically compatible carrier.

8. A method of preventing or inhibiting virus infection of humans or other animals, comprising introducing into the circulatory system of the human or other animal to be treated by transdermal penetration a composition consisting essentially of at least one C-20 to C-26 aliphatic alcohol in a physiologically compatible carrier.

9. A physiologically compatible solution suitable for injection into humans or other animals to prevent or treat disease in such humans or other animals consisting essentially of at least one C-20 to C-26 aliphatic alcohol in a physiologically compatible injectable carrier.

10. A physiologically compatible transdermal medication for introduction through the mucous membranes into humans or other animals consisting essentially of at least one C-20 to C-26 aliphatic alcohol and a penetration enhancer.

11. The method of claim 1 wherein composition consists essentially of C-22 aliphatic alcohol in a physiologically compatible carrier.

12. The method of claim 2 wherein composition consists essentially of C-22 aliphatic alcohol in a physiologically compatible carrier.

13. The method of claim 3 wherein composition consists essentially of C-22 aliphatic alcohol in a physiologically compatible carrier.

14. The method of claim 4 wherein composition consists essentially of C-22 aliphatic alcohol in a physiologically compatible carrier.

15. The method of claim 5 wherein composition consists essentially of C-22 aliphatic alcohol in a physiologically compatible carrier.

16. The method of claim 6 wherein composition consists essentially of C-22 aliphatic alcohol in a physiologically compatible carrier.

17. The method of claim 7 wherein composition consists essentially of C-22 aliphatic alcohol in a physiologically compatible carrier.

18. The method of claim 8 wherein composition consists essentially of C-22 aliphatic alcohol in a physiologically compatible carrier.

* * * * *